United States Patent [19]

Beyer, Jr.

[11] Patent Number: 5,110,817

[45] Date of Patent: * May 5, 1992

[54] METHOD FOR CONTROLLING AND/OR LOWERING SERUM TRIGLYCERIDE AND/OR CHOLESTEROL LEVELS IN MAMMALS

[76] Inventor: Karl H. Beyer, Jr., P.O. Box 387, 1001 Gypsy Hill Rd., Penllyn, Pa. 19422

[*] Notice: The portion of the term of this patent subsequent to Apr. 24, 2007 has been disclaimed.

[21] Appl. No.: 472,878

[22] Filed: Jan. 31, 1990

Related U.S. Application Data

[63] Continuation of Ser. No. 260,947, Oct. 21, 1988, Pat. No. 4,920,123.

[51] Int. Cl.$^5$ ............................................. A61K 31/495
[52] U.S. Cl. ...................................... 514/255; 514/824
[58] Field of Search .................................. 514/255, 824

[56] References Cited

U.S. PATENT DOCUMENTS 4,604,394  8/1986  Kaczorowski et al. ............ 514/255
4,920,123  4/1990  Beyer ................................... 514/255

FOREIGN PATENT DOCUMENTS 2205099  11/1988  United Kingdom .

OTHER PUBLICATIONS

Ambrogi et al, Eur. J. Med. Chem. vol. 15, No. 2, Mar.-/Apr. 1980, pp. 157-163.
H. Regal et al, Drugs Exptl. Clin. Res., vol. 10, No. 8-9, 1984, pp. 621-625.
Chemical Abstracts; vol. 78 (1973) #106186r; Pinelli et al.
Chemical Abstracts; vol. 73 (1970) #98986f; Uchimaru et al.
Chemical Abstracts; vol. 73 (1970) #33695r; Tamasi et al.

Primary Examiner—Frederick E. Waddell
Assistant Examiner—Kimberly R. Jordan
Attorney, Agent, or Firm—Oblon, Spivak, McClelland, Maier & Neustadt

[57] ABSTRACT

A method for controlling and/or reducing a patient's serum cholesterol and/or triglyceride level is disclosed.

5 Claims, 2 Drawing Sheets

METHOD FOR CONTROLLING AND/OR LOWERING SERUM TRIGLYCERIDE AND/OR CHOLESTEROL LEVELS IN MAMMALS

This is a continuation of application Ser. No. 07/260,947, filed on Oct. 21, 1988 now U.S. Pat. No. 4,920,123.

BACKGROUND OF THE INVENTION

1. Field of the Invention

The present invention relates to methods for controlling and/or lowering serum triglyceride and/or cholesterol levels in mammals.

2. Discussion of the Background

Coronary heart disease (CHD) and stroke combine to take by far the greatest toll of life among the more frequent causes of death. Actually, CHD, alone, exceeds other causes of death.

The advent of particularly saluretic antihypertensive therapy has lowered the incidence of stroke impressively, but not the incidence of death from CHD. The fact that commonly prescribed antihypertensive thiazides increase triglyceride blood levels and increase hypercholesterolemia in some patients may contribute to this risk of a greater mortality from CHD when such therapy is employed. Similarly, the nephrology literature recognizes hypertriglyceridemia as a likely risk factor for myocardial infarction in chronic renal failure patients. The Framingham Study has recently affirmed triglycerides as a primary risk factor.

Hypercholesterolemia, particularly increased low density lipoproteinemia-cholesterol (LDL) and hypertriglyceridemia, associated with particularly very low density lipoproteinemia-cholesterol (VLDL), may coexist in the atherosclerotic patient or may exist separately. Likewise, some forms of therapy are better suited to reduction of one or another type of hyperlipidemia. For instance, the bile acid sequestrants, such as cholestyramine and cholestipol decrease LDL cholesterol but are not effective in lowering triglyceridemia. The dosage of 4 or 5 grams taken as a suspension orally twice a day limits their acceptance by the patient. Nicotinic acid is effective and safe for lowering particularly triglyceridemia, but the dosage of 1.5 to 3 grams/day must be worked up to gradually to minimize the flushing and itching of skin which frequently cannot be tolerated by the patient.

Inhibitors of 3-hydroxy-3-methylglutaryl CoA reductase are particularly effective in primary hypercholesterolemia. Of these, lovastatin has recently become the first marketed, so that reduction of CHD incidence by these agents has not been established; nor are these primarily trigylceride-lowering agents. Clofibrate and gemfibrozil are fibric acid derivatives. The latter agent is the newer and may be the safer. It has been reported to be capable of lowering triglyceride and/or LDL cholesterol levels.

In the adult person, hypercholesterolemia usually is attended by hypertension. Whereas a low salt diet may reduce high blood pressure somewhat, it does not reduce hypercholesterolemia. Likewise, a low protein diet employed for reduction of hyperuremia in the patient having chronic progressive renal failure does not reduce hypertriglyceridemia; neither does any form of dialysis treatment.

Coadministration of antihypertensive therapy per se with inhibitors of hypercholesterolemia or hypertriglyceridemia is customary even though the more generally prescribed thiazides or beta-adrenergic blocking agents for hypertension may offset in some measure by their own effects the desired reduction in lipoprotein blood levels, and so are counterproductive with respect to lowering cholesterol and triglyceride blood levels.

Cragoe et al., U.S. Pat. No. 3,313,813, describe 3-amino-5,6-disubstituted-pyrazinoyl guanidines and their use as diuretic, natriuretic agents which selectively enhance the excretion of sodium ions without causing an increase in excretion of potassium ions. Amiloride, a compound of the formula

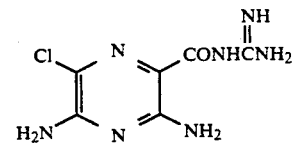

is one of the compounds disclosed in Cragoe et al and the most successfully used compound disclosed in that publication, has been found to possess no advantageous activity towards the control or lowering of serum triglyceride and/or cholesterol levels. A study by Leary et al published in "SA Mediese Tydskrif" (1981), pp. 381-384, reports that the administration of a combination of amiloride and hydrochlorothiazide does not change the plasma cholesterol level in a patient and actually increases the serum triglyceride level.

There is thus a strongly felt need for new methods for the control and/or lowering of serum triglyceride and/or cholesterol levels in mammals, e.g. humans.

SUMMARY OF THE INVENTION

Accordingly, it is an object of this invention to provide a method for controlling and/or lowering the serum triglyceride level in a mammal, e.g. a human.

It is another object of this invention to provide a method for controlling and/or lowering the cholesterol level in a mammal, e.g. a human.

These objects and other objects which will become apparent from the description of the invention given hereinbelow have been discovered by the inventor to be all satisfied by administering to a patient, in need thereof, of an effective amount of a compound of the formula (I)

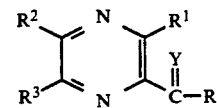

wherein

Y is O or NH,

R is OH, NHCONR$^4$R$^5$; or N=C(NR$^4$R$^5$)2; where
  R$^4$ and R$^5$ are each independently selected from the group consisting of hydrogen; C$_{1-10}$ alkyl, straight or branched chain; aryl C$_{1-4}$ alkyl; mono- or disubstituted aryl C$_{1-4}$ alkyl where the substituents are fluoro, chloro, bromo, iodo, trifluoromethyl, or C$_{1-10}$ alkyl, straight or branched chain;

R$^1$ and R$^2$ are each independent selected from the group consisting of hydrogen, amino, and mono- or disubstituted amino where the substituents are C$_{1-10}$ alkyl, straight or branched chain, or C$_{3-8}$ cycloalkyl;

provided that $R^1$ and $R^2$ may not both be amino or substituted amino; and $R^3$ is hydrogen, trifluoromethyl; fluoro; chloro; bromo; or iodo; or a pharmaceutically acceptable salt thereof.

BRIEF DESCRIPTION OF THE FIGURES

A more complete appreciation of the invention and many of its attendant advantages will be readily obtained as the same becomes better understood by reference to the following detailed description when considered in connection with the accompanying drawings, wherein.

DETAILED DESCRIPTION OF THE PREFERRED EMBODIMENTS

Figure 1:
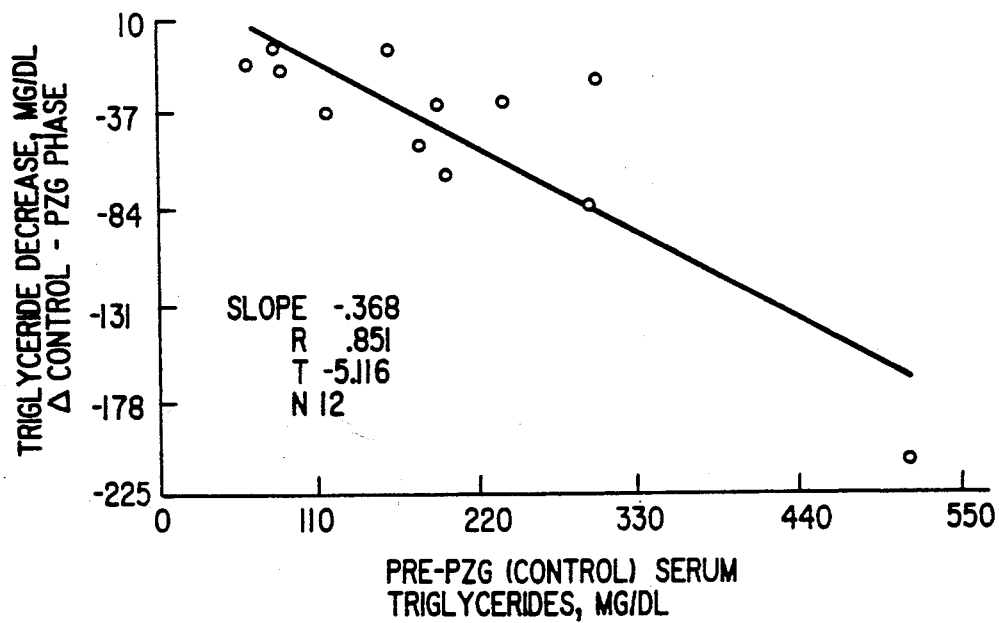
FIG. 1 illustrates that with the method of the present invention, the greater the azotemic patients' pre-drug triglyceride serum concentration, the greater the reduction thereof induced by pyrazinoylguanidine (PZG).

While studying pyrazinoylquanidines and their 3-amino analogs as inhibitors of urea and salt reabsorption by the kidney (i.e., as hyperuretic and saluretic agents), the inventor discovered that in addition to lowering urea blood levels and decreasing hypertensive blood pressure these compounds, and in particular the representative pyrazinoylguanidine (PZG), decreased blood serum concentration of triglycerides and cholesterol significantly.

The significance of the present discovery is that a single drug, the compounds of formula (I), and pyrazinoylguanidine by example, have been found by the inventor to reduce hypertensive blood pressure and urea serum concentration whether or not the two conditions coexist in the same patient (i.e., in essential hypertension or in renal insufficiency). At the same effective dosage (of 300 mg/d to 600 mg, b.i.d.), the compounds of formula (I) reduce significantly triglyceride and cholesterol serum concentration; both serious risk factors that contribute to the high incidence of coronary heart disease and stroke in addition to systemic arteriosclerosis and chronic progressive renal failure. The drug is well tolerated by the patient at useful dosages, and its effects are reversible.

In a preferred embodiment, the compound used in the method of the invention has the formula (II)

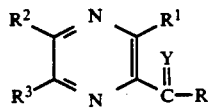

wherein:
Y is O,
R is OH, $NHCONR^4R^5$; or $N=C(NR^4R^5)_2$; where $R^4$ and $R^5$ are each independently selected from the group consisting of hydrogen; $C_{1-10}$ alkyl, straight or branched chain; aryl $C_{1-4}$ alkyl; mono- or disubstituted aryl $C_{1-4}$ alkyl where the substituents are fluoro, chloro, bromo, iodo, or $C_{1-10}$ alkyl, straight or branched chain;

$R^1$ and $R^2$ are each independent selected from the group consisting of hydrogen, amino, and mono- or disubstituted amino where the substituents are $C_{1-10}$ alkyl, straight or branched chain, or $C_{3-8}$ cycloalkyl; provided that $R^1$ and $R^2$ may not both be amino or substituted amino; and $R^3$ is hydrogen, trifluoromethyl; fluoro; chloro; bromo; or iodo; or pharmaceutically acceptable salts thereof.

In another preferred embodiment, the compound used has the following formula (III):

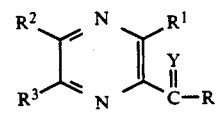

wherein
Y is O;
R is $N=C(NR^4R^5)_2$; where $R^4$ and $R^5$ are each independently selected from the group consisting of hydrogen; $C_{1-10}$ alkyl, straight or branched chain; aryl $C_{1-4}$ alkyl; mono- or disubstituted aryl $C_{1-4}$ alkyl where the substituents are fluoro, chloro, bromo, iodo, or $C_{1-10}$ alkyl, straight or branched chain;

$R^1$ and $R^2$ are each independent selected from the group consisting of hydrogen, amino, and mono- or disubstituted amino where the substituents are $C_{1-10}$ alkyl, straight or branched chain, or $C_{3-8}$ cycloalkyl; provided that $R^1$ and $R^2$ may not both be amino or substituted amino; and $R^3$ is hydrogen, trifluoromethyl; fluoro; chloro; bromo; or iodo; and pharmaceutically acceptable salts thereof.

Most preferred compounds of the present invention are those wherein for the compound of Formula (I), Y is O or NH; one of $R^1$ and $R^2$ is hydrogen or amino and the other is hydrogen; and $R^3$ is hydrogen. Particularly preferred compounds of Formula (I) are the following: pyrazinoylguanidine; and 3-aminopyrazinoylguanidine.

As should be noted by the structure of the preferred compounds of the present invention, the present compounds are distinguished from amiloride by the fact that they possess a low level of substitution. Amiloride is characterized by having a heterocycle substituted by two amino substituents, one chloro substituent, and one $-CONHC(=NH)NH_2$ substituent.

While the present invention provides for the administration of the compounds of Formulae (I), (II) or (III), it should be recognized that since these are pharmaceutical compounds it is conceivable that it is in fact one of the metabolites of these compounds which is directly responsible for the serum and triglyceride control or lowering effect discovered by the inventor.

The Formulae (I), (II) and (III) compounds can be used in the form of salts derived from inorganic or organic acids. Included among such salts are the following: adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinagte, persulfate, 3-phenylpropionate, picrate, pivalate, propionate, succinate, tartrate, thiocyanate, tosylate and undecanoate.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

For these purposes the combinations of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rabbits, rats, horses, dogs, cats, etc., the combinations of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets containing the active ingredient in admixture with non-toxic pharmaceutically acceptable excipients which are suitable for manufacture of tablets may be used. These excipients may be, for examplee, inert diluents, such as calcium carbonate, sodium carbonate, lactose, calcium phosphate or sodium phosphate; granulating and disintegrating agents, for example maize starch, or alginic acid; binding agents, for example starch, gelatin or acacia, and lubricating agents, for example magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The combinations of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the active ingredient are employed.

For the compounds of Formulae (I), (II) or (III), dosage levels of the order of 50 to 1200 mg. per day are useful in the treatment of the above indicated conditions. For example, a patient's high serum cholesterol level or high triglyceride level is effectively treated by the administration of from about 1.0 to 15 mg. of a compound of Formulae (I), (II) or (III) per kilogram of body weight per day. Advantageously from about 2 to about 15 mg. per kilogram of body weight and especially from about 3 to about 10 mg. per kilogram daily dosage produces highly effective results.

The amount of active ingredient that may be combined with the carrier materials to produce a single dosage form will vary depending upon the host treated and the particular mode of administration. For example, a formulation intended for the oral administration of humans may contain from 25 to 750 mg of active agent compounded with an appropriate and convenient amount of carrier material which may vary from about 5 to about 95 percent of the total composition. Dosage unit forms will generally contain between from about 25 to about 500 mg. of active ingredient.

It will be understood, however, that the specific dose level for any particular patient will depend upon a variety of factors including the activity of the specific compound employed, the age, body weight general health, sex, diet, time of administration, route of administration, and the severity of the particular disease undergoing therapy.

The compounds of Formulae (I), (II) or (III) utilized in the present invention are active on oral as well as parenteral administration.

The pyrazinoic acid derivatives utilized in the present invention may be prepared in accordance with well known procedures, for example those described in U.S. Pat. No. 3,313,813.

Other features of this invention will become apparent in the course of the following descriptions of exemplary embodiments which are given for illustration of the invention and are not intended to be limiting thereof.

As illustrated for mild hypertensive patients, the onset of PZG reduction of serum triglyceride levels is prompt, occurring within 24 h of a single dose. PZG is effective regardless of the range of triglyceride serum concentrations among the patients, and the magnitude of PZG effect is dose related as shown by the data tabulated in Table 1.

Table 2 compares the triglyceride serum concentration effects of PZG (dosage 300 to 600 mg, b.i.d., p.o., mean of 3 or 5 determinations over 3 weeks) and hydrochlorothiazide (HCT) (dosage 25 or 50 mg, b.i.d., p.o., mean of 3 or 5 determinations over 3 week period) with the mean of their 3-week corresponding control periods without regard for range of systemic blood pressure or renal function. PZG lowered triglyceride serum concentration significantly (P 0.012), and HCT significantly increased serum triglycerides (P 0.005).

Figure 2:
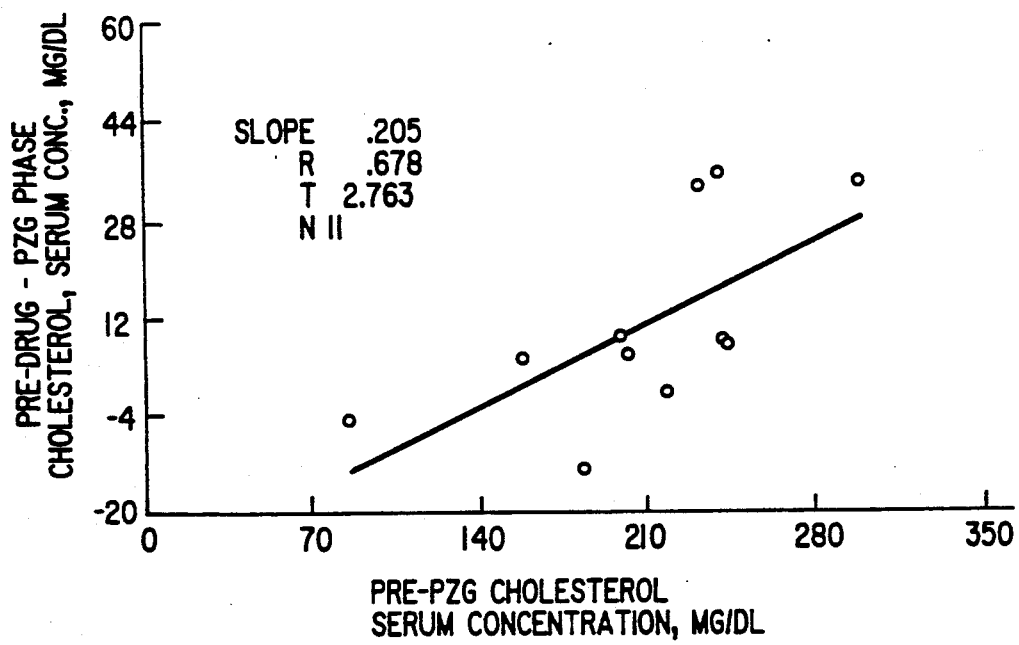
FIG. 2 illustrates that with the method of the present invention, the greater the azotemic patients' pre-drug cholesterol serum concentration, the greater reduction thereof by PZG.

Table 3 relates PZG and HCT administration to cholesterol serum concentration, as for the comparisons in Table 2. PZG significantly lowered serum cholesterol concentration whether all cholesterol values were compared with corresponding controls (P 0.011) or only cholesterol values exceeding 200 mg/dl were used for the comparison (P 0.018). Plotted as linear regression curves it is seen that the greater the patient's pre-drug triglyceride or cholesterol serum concentration the greater the reduction thereof by PZG administration, FIGS. 1 and 2.

Figure 3:
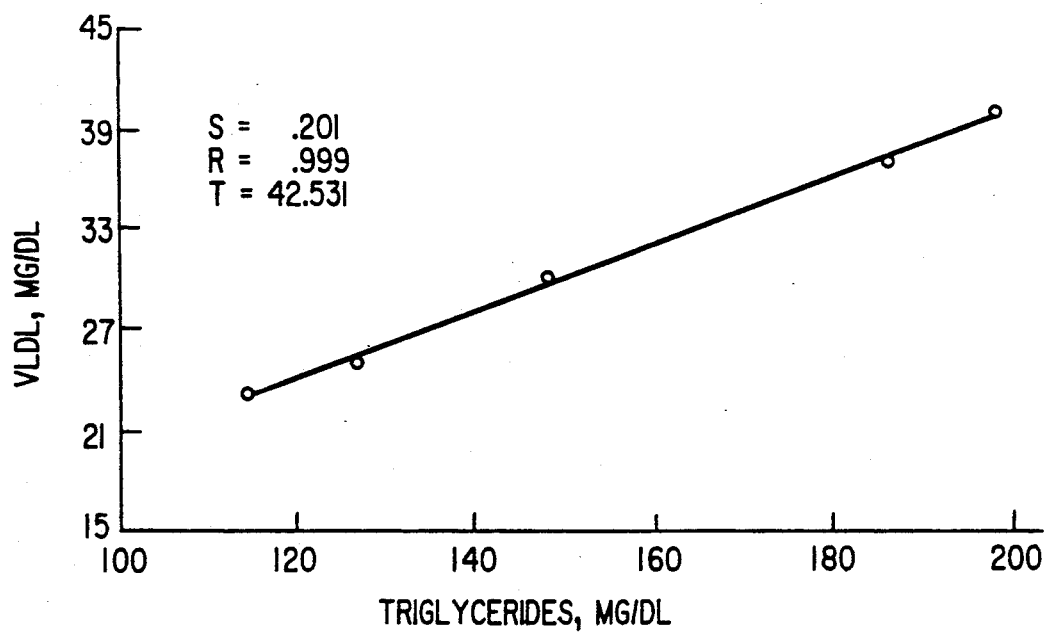
FIG. 3 illustrates the relation between very low density lipoproteins (VLDL) to serum triglycerides during PZG administration.
Figure 4:
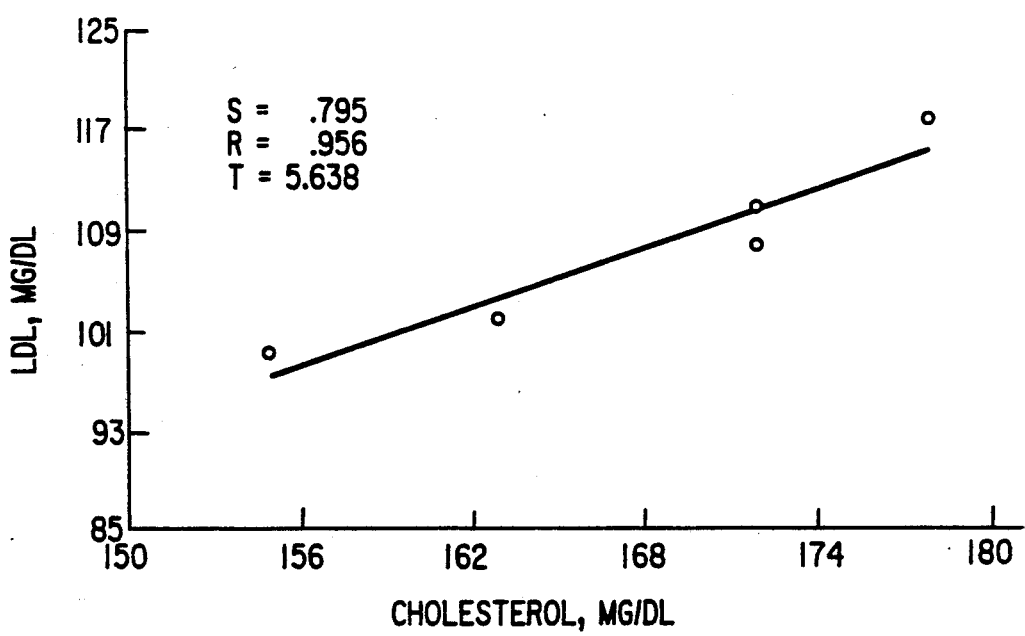
FIG. 4 illustrates the relation, provided by the present invention, between low density lipoprotein (LDL) to total serum cholesterol during PZG administration.

Likewise, during PZG administration the reduction in serum triglycerides and VLDL-cholesterol is highly correlated (r=0.999, FIG. 3) and so is the correlation between falling total cholesterol and LDL-cholesterol serum levels as influenced by PZG administration (r=0.956, FIG. 4).

TABLE 1

TRIGLYCERIDES. RELATIONSHIP OF PZG DOSAGE TO TRIGLYCERIDE SERUM CONCENTRATION, MG/DL, 24 H AFTER FIRST DOSE. HYPERTENSIVE PATIENTS

| PT | PZG, 400 MG/D | | | PZG, 800 MG/D | | |
|---|---|---|---|---|---|---|
| | CONTROL | D1 | % CHANGE | CONTROL | D1 | % CHANGE |
| 1 | 180 | 183 | +2 | 204 | 147 | −28 |
| 2 | 91 | 48 | −47 | 111 | 52 | −53 |
| 3 | 105 | 61 | −42 | 81 | 60 | −26 |
| 4 | 340 | 162 | −52 | 410 | 191 | −53 |
| 5 | 189 | 170 | −10 | 175 | 92 | −47 |
| $\bar{X}$ | 181 | 125 | | 196 | 108 | |
| % DECREASE | | | 31 | | | 45 |

TABLE 2

TRIGLYCERIDES: EFFECT OF PZG AND HYDROCHLOROTHIAZIDE (HCT) ON TRIGLYCERIDE SERUM LEVELS. T-TEST COMPARISON OF MEAN OF PRE-DRUG VALUES WITH CORRESPONDING MEAN VALUES DURING DRUG ADMINISTRATION WITHOUT REGARD TO DOSAGE OR PRE-DRUG TRIGLYCERIDE CONCENTRATION, MG/DL.

| PATIENT | $\bar{x}$ PRE-PZG | $\bar{x}$ PZG-PHASE | $\bar{x}$ PRE-HCT | $\bar{x}$ HCT-PHASE |
|---|---|---|---|---|
| M.F. | 149 | 164 | 115 | 134 |
| | 198 | 131 | — | — |
| S.C. | 477 | 194 | 403 | 485 |
| D.R. | 64 | 50 | 64 | 88 |
| G.W. | 301 | 282 | 228 | 330 |
| L.M. | 296 | 216 | 260 | 368 |
| T.L. | 181 | 128 | 114 | 257 |
| H.N. | 515 | 312 | 454 | 603 |
| J.W. | 238 | 208 | 197 | 183 |
| E.K. | 78 | 76 | 62 | 86 |

TABLE 2-continued

TRIGLYCERIDES: EFFECT OF PZG AND HYDRO-
CHLOROTHIAZIDE (HCT) ON TRIGLYCERIDE SERUM
LEVELS. T-TEST COMPARISON OF MEAN OF
PRE-DRUG VALUES WITH CORRESPONDING MEAN
VALUES DURING DRUG ADMINISTRATION WITHOUT
REGARD TO DOSAGE OR PRE-DRUG
TRIGLYCERIDE CONCENTRATION, MG/DL.

| PA-TIENT | $\bar{x}$ PRE-PZG | $\bar{x}$ PZG-PHASE | $\bar{x}$ PRE-HCT | $\bar{x}$ HCT-PHASE |
|---|---|---|---|---|
| B.S. | 87 | 70 | 66 | 73 |
| R.B. | 118 | 81 | 118 | 127 |
|  | 117 | 89 | — | — |
| W.B. | 194 | 162 | 161 | 189 |
|  | 177 | 142 | — | — |
| $\bar{x}$ | 213 | 154 | 187 | 244 |
| S.E. | 35 | 20 | 38 | 49 |
| P | PRE-PZG VS PZG PHASE .012 | | PRE HCT VS HCT PHASE .005 | |

TABLE 3

EFFECT OF PZG AND HYDROCHLOROTHIAZIDE (HCT)
ON CHOLESTEROL SERUM LEVELS
T-TEST COMPARISON OF MEAN OF PRE-DRUG
VALUES WITH CORRESPONDING MEAN VALUES
DURING DRUG ADMINISTRATION WITHOUT REGARD
TO DOSAGE (1) AT ALL CHOLESTEROL CONTROL
SERUM CONCENTRATIONS AND (2) AT SINGLE
200 MG/DL OR GREATER VALUES IN THE
PRE-DRUG PHASE.

| PA-TIENT | $\bar{x}$ PRE-PZG | $\bar{x}$ PZG-PHASE | $\bar{x}$ PRE-HCT | $\bar{x}$ HCT-PHASE |
|---|---|---|---|---|
| M.F. | 219 | 218 | 205 | 217 |
|  | 233 | 198 |  |  |
| S.C. | 160 | 154 | 154 | 162 |
| D.R. | 87 | 92 | 89 | 95 |
| G.W. | 243 | 233 | 249 | 272 |
| L.M. | 240 | 203 | 235 | 252 |
| T.L. | 203 | 197 | 226 | 208 |
|  | 202 | 195 |  |  |
| H.N. | 300 | 264 | 272 | 262 |
| J.W. | 184 | 196 | 193 | 187 |
| B.S. | 245 | 236 | 252 | 264 |
| E.K. | 170 | 168 | 169 | 177 |
| R.B. | 181 | 167 | 151 | 181 |
|  | 170 | 149 |  |  |
| W.B. | 208 | 206 | 213 | 193 |
|  | 193 | 194 |  |  |
| $\bar{x}$ (all values) | 202 | 192 | 201 | 206 |
| S.E. | 12 | 10 | 15 | 15 |
| P | PRE-PZG VS PZG .011 (DF 16) | | PRE-HCT VS HCT .278 (DF 11) | |
| *$\bar{x}$, = 200 | 239 | 220 | 236 | 238 |
| S.E. | 12 | 10 | 9 | 9 |
| P | PRE-PZG VS PZG .018 (DF 7) | | PRE-HCT VS HCT .742 (DF 6) | |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for treating hypertriglyceridemia in a patient, comprising administering to said patient an effective amount of at least one compound of formula (I):

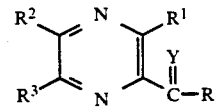

wherein
Y is O or NH,
R is OH, NHCONR$^4$R$^5$; or N=C(NR$^4$R$^5$)$_2$; where R$^4$ and R$^5$ are each independently selected from the group consisting of hydrogen; C$_{1-10}$ alkyl, straight or branched chain; aryl C$_{1-4}$ alkyl; mono- or disubstituted aryl C$_{1-4}$ alkyl where the substituents are fluoro, chloro, bromo, iodo, or C$_{1-10}$ alkyl, straight or branched chain;
R$^1$ and R$^2$ are each independent selected from the group consisting of hydrogen, amino, and mono- or di-substituted amino where the substituents are C$_{1-10}$ alkyl, straight or branched chain, C$_{3-8}$ cycloalkyl; provided that R$^1$ and R$^2$ may not both be amino or substituted amino; and
R$^3$ is hydrogen, trifluoromethyl; fluoro; chloro; bromo; or iodo; or a pharmaceutically acceptable salt thereof.

2. The method of claim 1, wherein Y is O.

3. The method of claim 1, wherein R is N=C(NR$^4$R$^5$)$_2$.

4. The method of claim 1, wherein said compound is pyrazinoylguanidine.

5. The method of claim 1, wherein said compound is 3-amino pyrazinoylguanidine.

* * * * *